United States Patent [19]

Beran et al.

[11] 4,182,883

[45] Jan. 8, 1980

[54] D-6-ALLYL-8-ERGOL-I-YLACETAMIDE

[75] Inventors: Miloš Beran; Jiří Křepelka; Miroslav Semonský; Karel Řežábek; Miroslav Šeda; Marie Aušková, all of Prague, Czechoslovakia

[73] Assignee: Spofa, United Pharmaceutical Works, Prague, Czechoslovakia

[21] Appl. No.: 857,994

[22] Filed: Dec. 6, 1977

[30] Foreign Application Priority Data

Dec. 6, 1976 [CS] Czechoslovakia ............... 7932/76

[51] Int. Cl.$^2$ ................. C07D 457/02; A61K 31/48
[52] U.S. Cl. ....................................... 546/67; 424/261
[58] Field of Search .............. 260/285.5; 424/261; 546/67

[56] References Cited

U.S. PATENT DOCUMENTS

| | | | |
|---|---|---|---|
| 3,920,664 | 11/1975 | Clemens et al. | 260/285.5 |
| 3,959,288 | 5/1976 | Bach et al. | 260/285.5 |
| 3,966,941 | 6/1976 | Semonsky et al. | 260/285.5 |
| 3,972,883 | 8/1976 | Arcau et al. | 260/285.5 |
| 4,064,130 | 12/1977 | Semonsky et al. | 260/285.5 |

FOREIGN PATENT DOCUMENTS

| | | | |
|---|---|---|---|
| 1439953 | 9/1965 | France | 260/285.5 |
| 86201 | 9/1957 | Netherlands | 260/285.5 |

OTHER PUBLICATIONS

Zabichy; The Chemistry of Amides; (1970) p. 119.
Hofmann; Die Mutterkornalkaloide; pp. 66–67 (1964).

*Primary Examiner*—Donald G. Daus
*Assistant Examiner*—Mary C. Lee

[57] ABSTRACT

A process is described for the preparation of novel 6 substituted derivatives of D-8-ergolin-I-ylacetamide and the pharmaceutically acceptable addition salts thereof. The described composition evidences superior antilactation and antinidation characteristics as compared with prior art compounds.

1 Claim, No Drawings

D-6-ALLYL-8-ERGOL-I-YLACETAMIDE

This invention relates to a process for the preparation of ergolin-I-ylacetamide derivatives and to the derivatives so produced. More particularly, the present invention relates to a process for the preparation of 6-substituted derivatives of D-8-ergolin-I-ylacetamide, the derivatives so produced and pharmaceutically acceptable addition salts thereof with organic and inorganic acids.

The compositions described herein and the addition salts thereof have been found during biological testing to evidence a significant inhibitory effect on the secretion of adenohypophysary prolactin in experimental animals, namely, Wister rats. This manifested itself by a decrease in the prolactin level in blood and, as a result, by markedly pronounced antilactation and antinidation effects.

The ergolin derivatives described are of the general formula

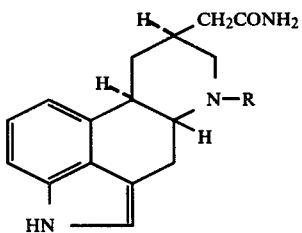

wherein R is an alkyl group having from 2-3 carbon atoms or an allyl group. The oral administration of slight doses of such derivatives result in the above-noted effects and suggest that these derivatives are the most potent inhibitors of the adenohypophysary prolactin secretion reported to date.

The ergolin derivatives identified as (1) above are conveniently prepared by (a) hydrolyzing nitriles of the formula,

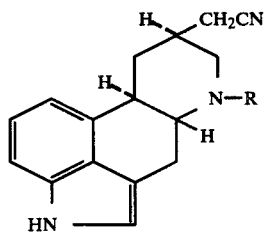

wherein R is an allyl group of 2-3 carbon atoms or an allyl group, to the corresponding carboxylic acids of the general formula

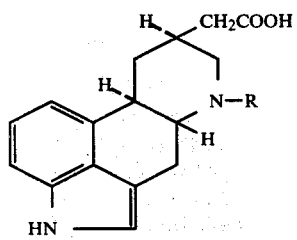

wherein R is represented as above.

Following, the carboxylic acid is esterified to yield a compound of the general formula

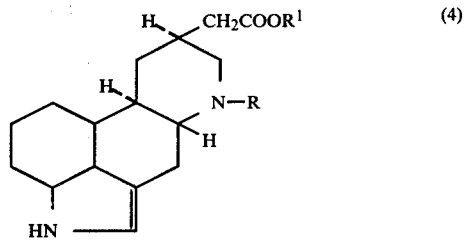

wherein R is as above and $R^1$ is an alkyl group having from 1-2 carbon atoms. The ester so obtained is next reacted with hydrazine to yield a corresponding hydrazide of the general formula

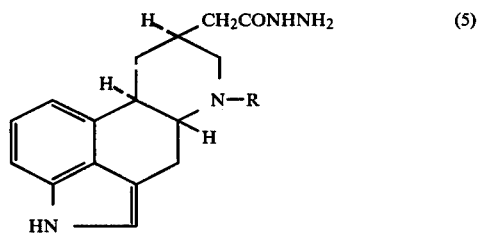

wherein R is as above. Finally, the hydrazide is converted by known techniques to the desired 6-substituted derivative of D-8-ergolin-I-ylacetamide of the formula denoted (1) above. Alternatively, bases of compound (1) may be reacted with non-toxic pharmaceutically acceptable inorganic or organic acids to yield the corresponding acid addition salts.

The nitrile hydrolysis described above is advantageously effected by means of an aqueous methanol or aqueous ethanol potassium hydroxide solution at the boiling temperature of the reaction mixture. The esterification reaction following hydrolysis is also conducted at the boiling temperature of the reaction mixture. However, this reaction desirably occurs in the presence of a methanol or ethanol hydrogen chloride solution.

Conversion of the noted esters to the corresponding hydrazides is attained by reaction thereof with hydrazinehydrate at the boiling temperature of the reaction mixture in a non-oxidizing ambient comprising an inert gas. A particularly useful procedure for attaining this end involves reacting the ester with commercial hydrazinehydrate solution (85%) under nitrogen.

The final step of hydrazide conversion to the desired amide may be effected either by the action of nitrous acid (liberated in situ from an alkali metal nitrite in an acidic aqueous medium) and the subsequent decomposition of the azides so formed with aqueous ammonia or, alternatively, by catalytic hydrogenolysis at the boiling point of the reaction mixture. The use of Raney nickel as the catalyst and/or a hydrogen carrier in an ethanolic medium is particularly suited for the invention again at the boiling temperature of the reaction mixture. The compounds of formula (1), may also be prepared from alkylchlorides which correspond with the carboxylic acids (3) or from other reactive derivatives, for example, anhydrides or mixed anhydrides or by methods known for the synthesis of peptides. However, it has been found that such preparative methods do not result in either the unexpectedly high yield or high purity of the final products of the invention.

Pharmaceutically, acceptable acid addition salts of the compounds of formula (1) are obtained by reacting one molequivalent of the base with at least one molequivalent of a non-toxic inorganic or organic acid in an inert solvent, preferably, methanol, ethanol, water or mixtures thereof.

Acids selected for this purpose include sulfuric, beta-naphthalenesulfonic, malonic, tartaric, succinic and the like. The normal tartarates, hydrogen maleates and beta-naphthalenesulfonates are satisfactorily soluble in water, stable and neutral in solution, so enhancing their convenience for conducting pharmacological tests and formulating suitable medinical dosages.

The ergolin derivates prepared as described can readily be processed with known pharmaceutical excipients and auxiliaries to yield highly potent and substantially harmless prolactin inhibiting compositions. The compositions are well suited for the treatment of anomalous states which require lowering the secretion of prolactin and/or the growth hormone, and also of syndroms necessitating regulation of the function of dopaminergic and serotoninergic structures of the central nervous system.

The biological testing, as noted above, evidences a significant inhibitory effect on the secretion of adenohypophysary prolactin in experimental animals. Thus, an oral dose of 0.025 mg/kg of D-6-n-propyl-8-ergolin-I-ylacetamide resulted in a prolactinemic decrease from 83.5 $\mu$g per ml. of blood serum in a control group of Wistor rates to as little as 6.3 $\mu$g/ml. during 9 hours upon the application to castrated female rats premedicated with an oestrogen. The prolactin level in the serum was determined by the standard radio-immuno assay method described by K. J. Graef et al in Endocrinology, Volume 98, Page 598, 1976.

The marked antinidation effect was evidenced upon a single oral dose of 30 $\mu$g/kg and 6 $\mu$g/kg of D-6-ethyl or D-6-n-propyl-8-ergoling-I-ylacetamide, respectively, administered in the form of an aqueous solution of the tartarate thereof on the fifth day following copulation. The entirety of the treated group of animals evidenced total blockage of pregnancy. Accordingly, it is clear that these two compounds evidence superior antinidation activity as compared with the known antinidation agent, D-6-methyl-8-ergolin-I-ylacetamide (described in U.S. Pat. No. 3,966,941). This superiority is of the order of from 10 to 40 times, respectively. Similarly, the antilactation effect of the D-6-ethyl and D-6-n-propyl-8-ergolin-I-ylacetamide as determined from the weight of suckling youngs of lactating rats expressed as a median effective dose (ED$_{50}$) of $\mu$g/kg administered orally on a daily basis was approximately 20 times greater than the above-noted known agent D-6-methyl-8-ergolin-I-ylacetamide. The evaluation of the antinidation and antilactation activity was done by the method of A. Cerny et al as described in Collection Czechoslovakian Chemical Communications, Volume 41, Page 1042, 1976 and by M. Auskova et al, Arzneimittel Forsch. 23, 617, 1973.

The ergolin derivatives of the invention are essentially non-toxic. Thus, the D-6-ethanol-8-ergolin-I-ylacetamide has an acute LD$_{50}$, in mice upon intravenous administration, as high as 38.5 mg/kg. Similarly, the D-6-n-propyl-8-ergolin-I-ylacetamide has an LD$_{50}$, intravenously in female rats, equal to 9.1 mg/kg. The compounds were administered in the form of the corresponding tartarate dissolved in a 0.9% aqueous sodium chloride solution. For comparative purposes, the LD$_{50}$ value of the prior art D-6-methyl-8-ergolin-I-ylacetamide as determined in female rats under identical conditions was 73 mg/kg. Thus, the therapeutical index of the D-6-n-propyl-8-ergolin-I-ylacetamide with respect to the antinidation activity of the prior art compound is approximately 5 times and with respect to the antilactation activity of the latter approximately 2.5 times more effective.

In addition to the foregoing the compounds herein described evidence a marked increase in the secretion of hypophysary gonadotropins. Thus, as shown by the standard unilateral ovarectomy method in rats (B. Benson et al, Endocrinology, 84, 369, 1969) both the 6-ethyl and the 6-n-propylanalogs of the prior art compound described above produce the same increase in the gonadotropin secretion as approximately 20 times higher doses of the reference composition.

The invention will be more fully understood by reference of the following exemplary embodiment. It will be appreciated by those skilled in the art that this example is merely for purposes of exposition and is not to be construed as limiting.

EXAMPLE

Methyl D-6-ethyl-8-ergolin-I-ylacetate

A mixture of 6.0 grams (0.0215 mole) of D-6-ethyl-8-cyano-methyl-ergolin I, 2.5 grams (0.384 mole) potassium hydroxide, 95 ml. of ethanol and 25 ml of water was refluxed for 24 hours under nitrogen. After standing for 20 hours at 5° C., the precipitated potassium D-6-ethyl-8-ergolin-I-ylacetate was filtered off, washed with ethanol and upon drying suspended in 265 ml. of methanol containing 6 grams of hydrogen chloride. The mixture was then refluxed for an additional 2 hours, evaporated under reduced pressure to dryness and the residue suspended in 1000 ml of water. Upon alkalization of the mixture with saturated aqueous sodium carbonate solution, the precipitated crude product was separated, washed with water, dried at 50° C. and purified by chromatography on a silica gel column with chloroform and 1% ethanol. Following, it was crystallized from a chloroform -n-hexane mixture (2:1) to yield the pure compound, methyl D-6-ethyl-8-ergolin-I-ylacetate melting at 178°–179° C. (alpha)$_D^{20}$ = −91.8° (C=0.34, pyridine).

D-6-Ethyl-8-ergolin-I-ylacetic acid hydrazide

A mixture of 2.6 grams (0.0083 mole) of methyl D-6-ethyl-8-ergolin-I-ylacetate and 52 ml 85% hydrazinehydrate was refluxed for 2½ hours under nitrogen. After standing 20 hours at 5° C., the precipitated hydrazide was filtered off, washed with water and upon drying purified by crystallization from a benzene-methanol mixture (1:1) to yield the pure hydrazide, m.p. 238°–241° C., (alpha)$_D^{20}$ = −91.1° (c=0.35, pyridine).

D-6-Ethyl-8-ergolin-I-ylacetamide

Procedure A

A solution of 2.0 g (0.0064 mole) of D-6-ethyl-8-ergolin-I-ylacetic acid hydrazide in 70 ml of 0.2 N hydrochloric acid was dropwise treated, under stirring and cooling to 0° C., with 5.74 ml 1 N sodium nitrile solution. After 10 minutes of standing at 0° C., the mixture was diluted with 20 ml 0.2 N hydrochloric acid. The precipitated D-6-ethyl-8-ergolin-I-ylacetic acid azide hydrochloride was filtered off, washed with 0.2 N hydrochloric acid and upon drying suspended in an excess of concentrated aqueous ammonia solution. After 20 hours of standing at room temperature, the precipitated D-6-ethyl-8-ergolin-I-ylacetamide was separated and purified by crystallization from a benzene - methanol mixture (1:1) to yield the ylacetamide melting at 263°–265° C., (alpha)$_D^{20}$ = −86.2° (c=0.23, pyridine).

Procedure B

A mixture of 2.0 g (0.0064 mole) D-6-ethyl-8ergolin-I-ylacetic acid hydrazide and 20 ml of a suspension of Raney nickel in 800 ml absolute ethanol was refluxed for one hour. Then, the catalyst was removed by filtration and the filtrate evaporated under reduced pressure to dryness. The so obtained D-6-ethyl-8-ergolin-I-ylacetamide was purified by crystallization from a benzene - methanol mixture (1:1) to yield the product having the same m.p. and (alpha)$_D^{20}$ as above.

Hydrogenmaleate of D-6-ethyl-8-ergolin-I-ylacetamide was prepared from 1 molequivalent of the base and 1.1 molequivalent of maleic acid in methanol and had m.p. 112°–115° C., (alpha)$_D^{20}$ = 41.5° (c−0.24, methanol).

Beta-Naphthalenesulfonate of the same base, prepared from 1 molequivalent of the base and 1.1 molequivalent of beta-naphtahlenesulfonic acid, in ethanol, melts at 234°–238° C., (alpha)$_D^{20}$ = −34.7° (c=0.1, methanol).

Hydrogentartarate, from 1 molequivalent of the base and 1.1 molequivalent of tartaric acid in ethanol, has a m.p. 232°–235° C., (alpha)$_D^{20}$ = −35.2° (c=0.19, methanol).

Normal tartarate, from 2 molequivalents of the base and 1 molequivalent of tartaric acid in ethanol, melts at 244°–250° C. and has (alpha)$_D^{20}$ = −37.6° (c−0.26, methanol).

The foregoing procedure was employed to prepare the following compounds:

D-6-n-propyl-8-ergolin-I-ylacetamide, m.p. 259°–261° C., (alpha)$_D^{20}$ = 66.7° (c=0.09, pyridine); normal tartarate, m.p. 228°–230° C., (alpha)$_D^{20}$ = −30.6° (c=0.18, methanol).

D-6-isopropyl-8-ergolin-I-ylacetamide, m.p. 279°–281° C., (alpha)$_D^{20}$ = −82.3° (c=0.17, pyridine).

D-6-allyl-8-ergolin-I-ylacetamide, m.p. 284°–286° C., (alpha)$_D^{20}$ = −90.5° (c=0.20, pyridine).

What is claimed is:

1. D-6-Allyl-8-ergolin-I-ylacetamide.